United States Patent
Niwa

(10) Patent No.: US 10,856,833 B2
(45) Date of Patent: Dec. 8, 2020

(54) RADIATION IMAGING APPARATUS COMPRISING A PROCESSING UNIT CONFIGURED TO SET A CONTROL TIMING OF A RADIATION SOURCE WITH RESPECT TO A WIRED OR WIRELESS COMMUNICATION WITH AN IMAGING CAPTURING UNIT

(71) Applicant: CANON KABUSHIKI KAISHA, Tokyo (JP)

(72) Inventor: Hiroaki Niwa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/185,496

(22) Filed: Nov. 9, 2018

(65) Prior Publication Data
US 2019/0145911 A1    May 16, 2019

(30) Foreign Application Priority Data
Nov. 15, 2017    (JP) .................................. 2017-220131

(51) Int. Cl.
  *A61B 6/00* (2006.01)
  *G01N 23/04* (2018.01)
  *H04N 5/32* (2006.01)

(52) U.S. Cl.
  CPC ................ *A61B 6/545* (2013.01); *A61B 6/40* (2013.01); *A61B 6/42* (2013.01); *A61B 6/4208* (2013.01); *A61B 6/4233* (2013.01); *A61B 6/4283* (2013.01); *A61B 6/44* (2013.01); *A61B 6/4411* (2013.01); *A61B 6/4452* (2013.01);
  (Continued)

(58) Field of Classification Search
  CPC ....... A61B 6/42; A61B 6/4208; A61B 6/4233; A61B 6/54; A61B 6/542; A61B 6/544; A61B 6/545; A61B 6/56; A61B 6/563; A61B 6/566; A61B 6/4283; A61B 6/44; A61B 6/4452; A61B 6/48; A61B 6/487; A61B 6/40; A61B 6/4411
  USPC ....... 378/62, 91, 98.8, 189, 96–98, 108–110, 378/196–198; 250/370.09
  See application file for complete search history.

(56) References Cited

U.S. PATENT DOCUMENTS

| 6,891,923 B2 * | 5/2005 | Tsujii | G01T 1/17 378/62 |
| 7,233,645 B2 * | 6/2007 | Feda | G01N 23/223 378/102 |

(Continued)

FOREIGN PATENT DOCUMENTS

| JP | 2010-081960 | 4/2010 |
| JP | 2013-188245 | 9/2013 |

(Continued)

*Primary Examiner* — Allen C. Ho
(74) *Attorney, Agent, or Firm* — Venable LLP

(57) ABSTRACT

A radiation imaging apparatus, comprising a radiation source configured to generate radiation, an image capturing unit configured to perform image capturing by detecting the radiation, and a processing unit configured to be communicable with the image capturing unit, wherein the processing unit performs a first operation which evaluates response time in communication with the image capturing unit, and a second operation which sets a control timing of the radiation source based on an evaluation result of the response time obtained in the first operation.

13 Claims, 9 Drawing Sheets

(52) U.S. Cl.
CPC .............. *A61B 6/48* (2013.01); *A61B 6/486* (2013.01); *A61B 6/487* (2013.01); *A61B 6/54* (2013.01); *A61B 6/544* (2013.01); *A61B 6/56* (2013.01); *A61B 6/563* (2013.01); *A61B 6/566* (2013.01); *G01N 23/04* (2013.01); *H04N 5/32* (2013.01)

(56) References Cited

U.S. PATENT DOCUMENTS

| | | | | |
|---|---|---|---|---|
| 7,382,859 | B2* | 6/2008 | Nokita | H04N 5/32 |
| | | | | 378/98.8 |
| 7,706,505 | B2* | 4/2010 | Tachikawa | G01N 23/223 |
| | | | | 378/42 |
| 7,847,277 | B2* | 12/2010 | Kito | A61B 6/4233 |
| | | | | 250/580 |
| 7,856,085 | B2* | 12/2010 | Hayashida | H04L 67/12 |
| | | | | 378/98 |
| 7,894,575 | B2 | 2/2011 | Tsubota et al. | |
| 8,130,909 | B2* | 3/2012 | Nishino | A61B 6/4283 |
| | | | | 250/370.09 |
| 8,275,835 | B2* | 9/2012 | Eguchi | A61B 6/4233 |
| | | | | 709/204 |
| 8,358,740 | B2* | 1/2013 | Nakatsugawa | A61B 6/102 |
| | | | | 378/116 |
| 8,483,456 | B2* | 7/2013 | Nagatsuka | A61B 5/08 |
| | | | | 382/128 |
| 8,576,087 | B2* | 11/2013 | Kamiya | A61B 6/4283 |
| | | | | 250/318 |
| 8,586,934 | B2* | 11/2013 | Nakatsugawa | G01T 1/2985 |
| | | | | 250/363.02 |
| 8,891,731 | B2* | 11/2014 | Schmitz | A61B 6/4405 |
| | | | | 378/116 |
| 8,956,045 | B2* | 2/2015 | Tajima | A61B 6/4283 |
| | | | | 378/145 |
| 9,044,194 | B2* | 6/2015 | Noji | A61B 5/08 |
| 9,078,624 | B2* | 7/2015 | Sugizaki | G01T 1/2928 |
| 9,103,922 | B2* | 8/2015 | Sung | G01T 1/2018 |
| 9,192,350 | B2* | 11/2015 | Hiroike | A61B 6/44 |
| 9,232,620 | B2* | 1/2016 | Tajima | H05G 1/42 |
| 9,351,699 | B2* | 5/2016 | Kuwabara | A61B 6/542 |
| 9,462,990 | B2* | 10/2016 | Kuwabara | A61B 6/542 |
| 9,538,969 | B2* | 1/2017 | Nishii | A61B 6/4233 |
| 9,569,829 | B2* | 2/2017 | Ohguri | H04N 5/2254 |
| 9,750,477 | B2* | 9/2017 | Kitagawa | A61B 6/542 |
| 9,757,086 | B2* | 9/2017 | Tezuka | A61B 6/54 |
| 9,788,809 | B2* | 10/2017 | Hiroike | A61B 6/4233 |
| 9,848,845 | B2* | 12/2017 | Tajima | H04N 5/32 |
| 9,931,092 | B2* | 4/2018 | Tajima | A61B 6/488 |
| 9,962,137 | B2* | 5/2018 | Iijima | A61B 6/4233 |
| 9,967,962 | B2* | 5/2018 | Imamura | A61B 6/542 |
| 9,984,306 | B2* | 5/2018 | Han | G06K 9/4642 |
| 10,004,469 | B2* | 6/2018 | Neumann | A61B 6/4014 |
| 10,052,071 | B2* | 8/2018 | Ishioka | A61B 6/5258 |
| 10,076,293 | B2* | 9/2018 | Sehnert | A61B 6/06 |
| 10,076,300 | B2* | 9/2018 | Lee | A61B 6/481 |
| 10,206,642 | B2* | 2/2019 | Hiroike | A61B 6/463 |
| 10,206,647 | B2* | 2/2019 | Hiroshige | A61B 6/4233 |
| 10,288,747 | B2* | 5/2019 | Tamura | G01T 1/17 |
| 10,368,826 | B2* | 8/2019 | Tamura | H05G 1/44 |
| 10,524,746 | B2* | 1/2020 | Maruta | A61B 6/4283 |
| 10,568,595 | B2* | 2/2020 | Hosoki | A61B 6/4233 |
| 10,617,304 | B2* | 4/2020 | Ohta | A61B 5/0071 |
| 10,667,670 | B2* | 6/2020 | Ohta | A61B 1/00011 |
| 2014/0241499 | A1 | 8/2014 | Tsuchiya | |

FOREIGN PATENT DOCUMENTS

| | | |
|---|---|---|
| JP | 2014-161454 | 9/2014 |
| JP | 2016-097115 | 5/2016 |

* cited by examiner

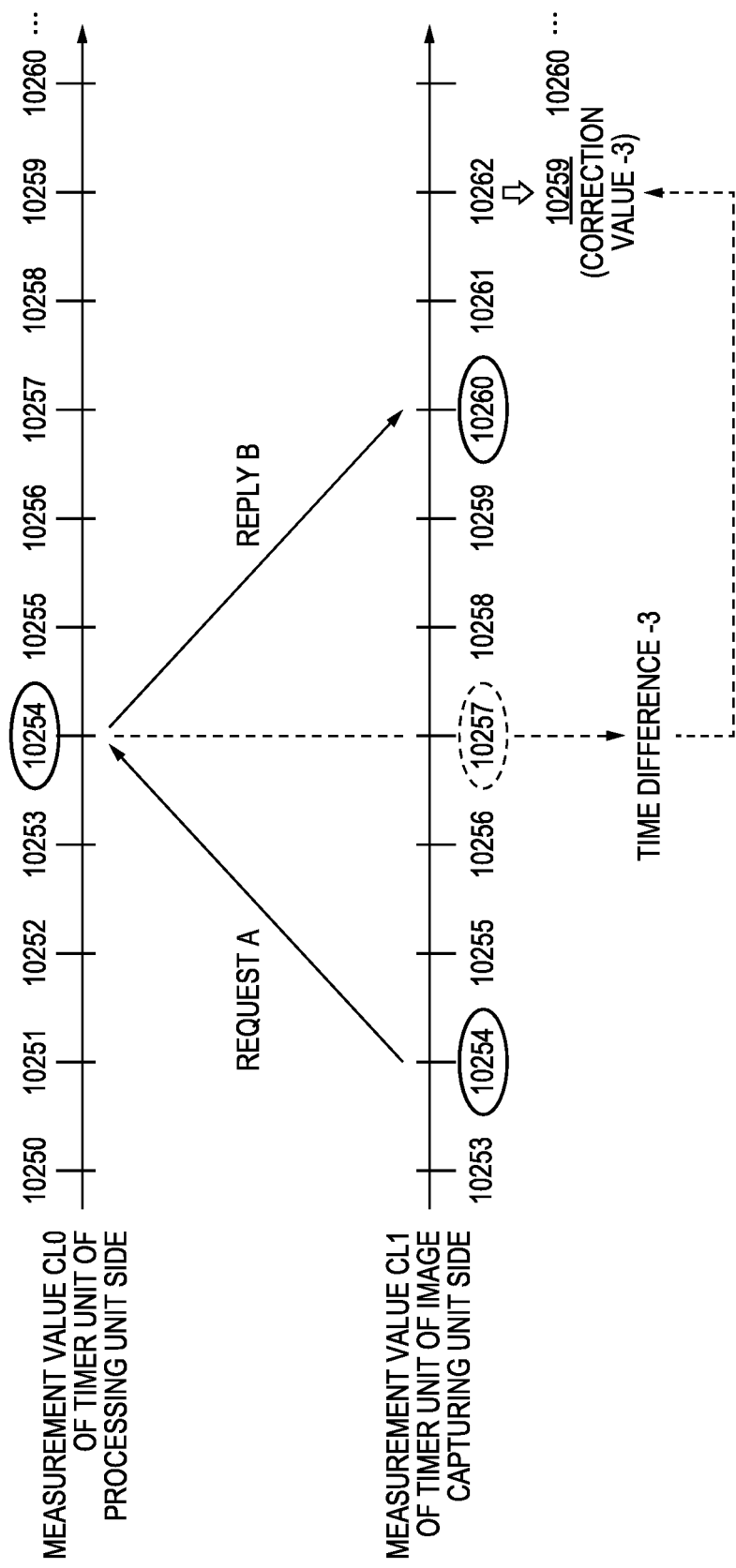

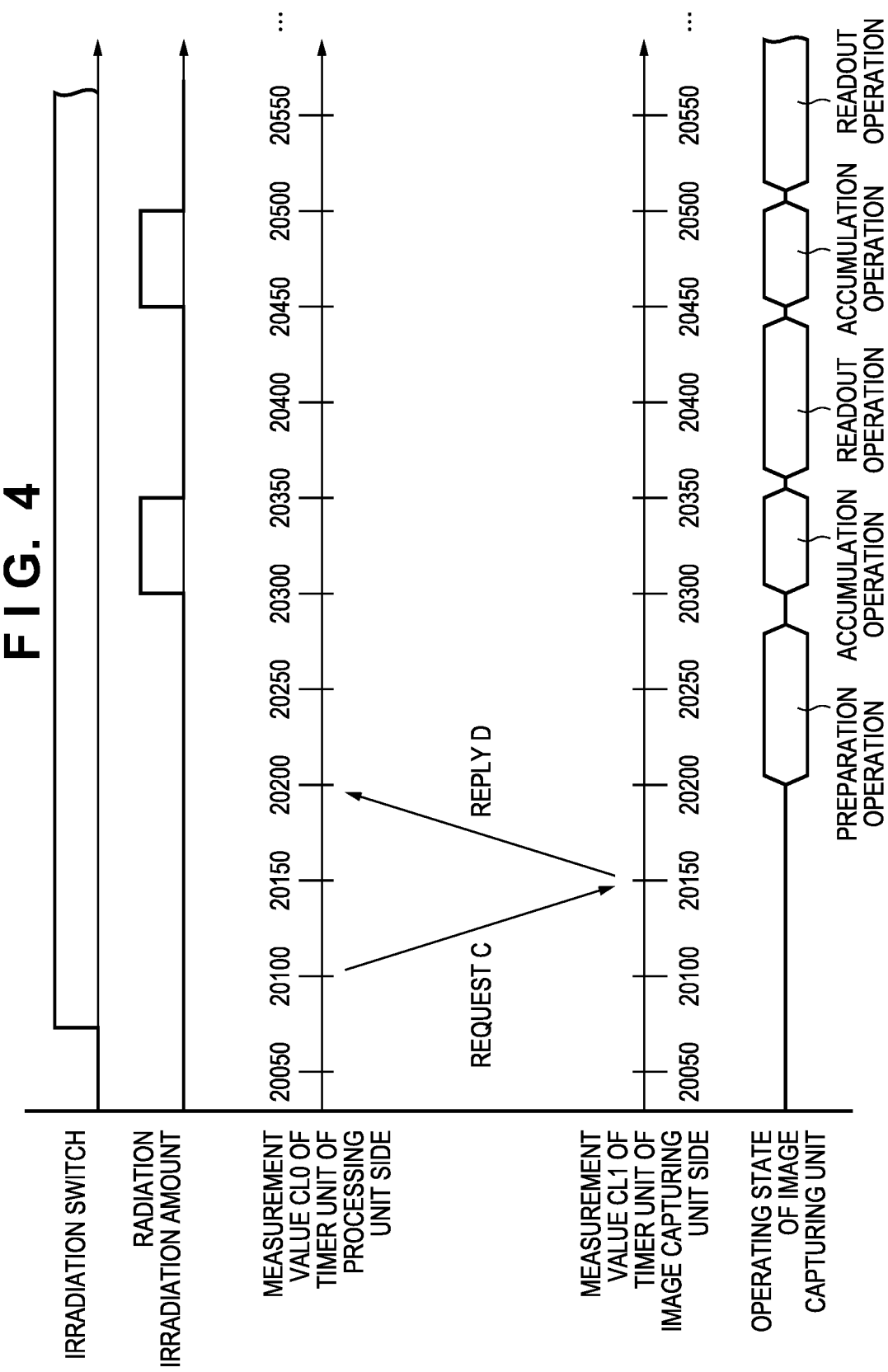

RADIATION IMAGING APPARATUS COMPRISING A PROCESSING UNIT CONFIGURED TO SET A CONTROL TIMING OF A RADIATION SOURCE WITH RESPECT TO A WIRED OR WIRELESS COMMUNICATION WITH AN IMAGING CAPTURING UNIT

BACKGROUND OF THE INVENTION

Field of the Invention

The present invention relates to a radiation imaging apparatus.

Description of the Related Art

Japanese Patent Laid-Open No. 2010-81960 describes an image capturing system including a radiation source for generating radiation, an image capturing apparatus for detecting the radiation from the radiation source and performing radiation image capturing, and a control apparatus for controlling the radiation source and the image capturing apparatus. The image capturing apparatus and the control apparatus include timer units, respectively. These timer units are synchronized with each other.

When two or more apparatuses are generally arranged in wired or wireless communication, a communication delay can occur between them. This also applies to the arrangement in Japanese Patent Laid-Open No. 2010-81960. That is, when performing radiation image capturing, the operation timings of the image capturing apparatus and the control apparatus can shift from each other due to this communication delay. For this reason, in the arrangement of Japanese Patent Laid-Open No. 2010-81960, when an unexpected events occurs such that the control apparatus drives the radiation source before the image capturing apparatus is set in an image capturing enable state, it may become difficult to appropriately perform radiation image capturing.

SUMMARY OF THE INVENTION

The present invention can control an image capturing operation corresponding to a communication delay and implement radiation image capturing appropriately.

One of the aspects of the present invention provides a radiation imaging apparatus, comprising a radiation source configured to generate radiation, an image capturing unit configured to perform image capturing by detecting the radiation, and a processing unit configured to be communicable with the image capturing unit, wherein the processing unit performs a first operation which evaluates response time in communication with the image capturing unit, and a second operation which sets a control timing of the radiation source based on an evaluation result of the response time obtained in the first operation.

Further features of the present invention will become apparent from the following description of exemplary embodiments with reference to the attached drawings.

BRIEF DESCRIPTION OF THE DRAWINGS

FIG. 2 is a view for explaining an example of a synchronization method between a processing unit and an image capturing unit;

FIG. 4 is a view for explaining an example of a scheduling mode;

DESCRIPTION OF THE EMBODIMENTS

Figure 1:
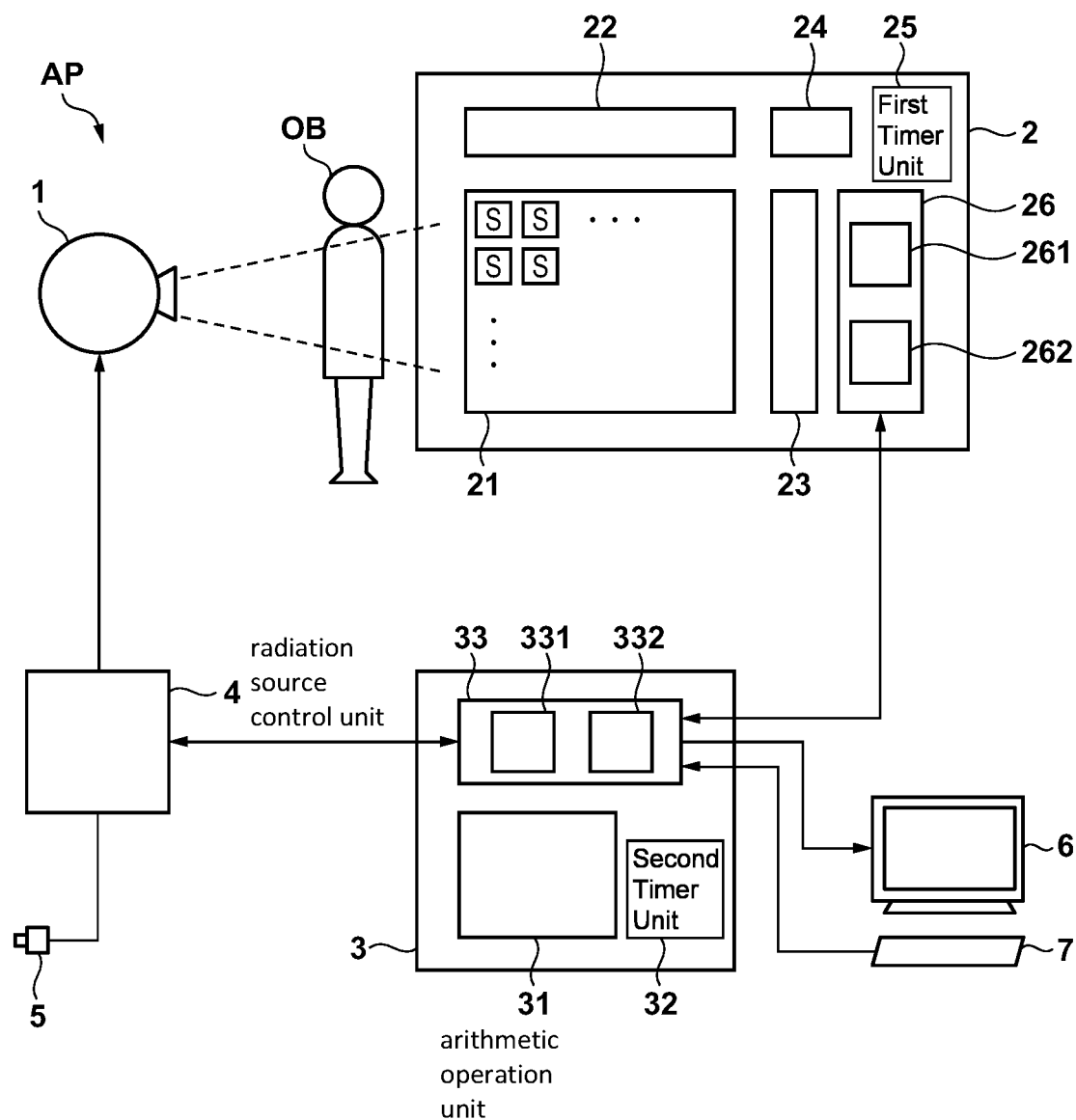
FIG. 1 is a block diagram for explaining an example of the system arrangement of a radiation imaging apparatus.

A preferred embodiment of the present invention will be described below with reference to the accompanying drawings. Note that each drawing is made for explaining the structure or arrangement, and the dimensions of the illustrated members do not necessarily reflect the actual dimensions. In addition, the same reference numerals denote the same members or constituent elements in these drawings, and a description of the overlapping contents will be omitted below.

FIG. 1 is a block diagram showing an arrangement example of a radiation imaging apparatus AP according to this embodiment. The radiation imaging apparatus AP includes a radiation source 1, an image capturing unit 2, a processing unit 3, a radiation source control unit 4, an irradiation switch 5, a display 6, and an input terminal 7. The radiation source 1 generates radiation. As radiation, an X-ray is typically used, but another electromagnetic wave such as an alpha-ray or beta-ray may be used.

The image capturing unit 2 includes a sensor array 21, a driving unit 22, a readout unit 23, an image capturing control unit 24, a timer unit 25, and a communication unit 26. In the sensor array 21, a plurality of sensors S capable of detecting radiation are arrayed to form a plurality of rows and a plurality of columns. This embodiment employs a method (a so-called indirect conversion method) of converting radiation into light and then converting the light into an electrical signal. Each sensor S includes a photoelectric conversion element such as a PIN sensor, a MIS sensor, or a CMOS image sensor. In this case, a scintillator is arranged above the sensor array 21. Note that as another embodiment, a method (a so-called direct conversion method) of directly converting radiation into an electrical signal may be employed.

A known vertical scanning circuit made from, for example, a decoder and a shift register can be used as the driving unit 22. The driving unit 22 can drive the plurality of sensors S on a row basis. A known horizontal scanning circuit formed from, for example, a shift register and a multiplexer can be used as the readout unit 23. On a column basis, the readout unit 23 reads out signals from the sensors S driven by the driving unit 22.

The image capturing control unit 24 performs the main arithmetic operation in the image capturing unit 2 and performs synchronous control of the elements such as the driving unit 22 and the readout unit 23 of the image capturing unit 2 and can implement the image capturing operation by the image capturing unit 2. For example, the image capturing control unit 24 causes the driving unit 22 to drive each sensor S, then causes the readout unit 23 to read out a signal from each driven sensor S, and generates image data based on the readout result.

In this embodiment, an ASIC (Application Specific Integrated Circuit) is used as the image capturing control unit 24. However, as another embodiment, another programmable semiconductor device may be used. Alternatively, the function of the image capturing control unit 24 may be implemented by a program or software using a CPU and a memory. That is, the function of the image capturing control unit 24 can be implemented by any one of hardware and software.

The timer unit 25 measures the time in the image capturing unit 2, and details of the timer unit 25 will be described later. The timer unit 25 allows synchronization between the image capturing unit 2 and the processing unit 3. Although the communication unit 26 will be described in detail later, it includes a wired communication unit 261 capable of performing wired communication using a LAN cable and a wireless communication unit 262 capable of performing wireless communication using Wi-Fi. The communication unit 26 can support various types of communication methods.

The processing unit 3 includes an arithmetic operation unit 31, a timer unit 32, and a communication unit 33 and integrally controls the overall operation of the radiation imaging apparatus AP. Although details of the processing unit 3 will be described later, for example, the processing unit 3 performs synchronization control of the remaining elements of the radiation imaging apparatus AP and can implement radiation image capturing of an object OB such as a patient. The arithmetic operation unit 31 performs main arithmetic operations in the processing unit 3. For example, the arithmetic operation unit 31 generates signals for driving the radiation source 1 and the image capturing unit 2 and receives image data from the image capturing unit 2, thereby performing image processing.

In this embodiment, a general-purpose computer is used as the arithmetic operation unit 31, and its function can be implemented by a CPU and a memory. As another embodiment, the arithmetic operation unit 31 may be implemented by a semiconductor device such as an ASIC. That is, the function of the arithmetic operation unit 31 can be implemented by any one of hardware and software.

The timer unit 32 measures the time in the processing unit 3, and details of the timer unit 32 will be described later. The timer unit 32 allows synchronization between the image capturing unit 2 and the processing unit 3. Although the communication unit 33 will be described in detail later, it includes a wired communication unit 331 capable of performing wired communication and a wireless communication unit 332 capable of performing wireless communication. The communication unit 33 can support various types of communication methods.

For example, the image capturing unit 2 and the processing unit 3 are communicably connected by the communication unit 26 and the communication unit 33. For example, if wired communication is used, the image capturing unit 2 and the processing unit 3 are connected to each other by a communication unit 251 and the wired communication unit 331. If wireless communication is used, the image capturing unit 2 and the processing unit 3 are connected to each other by a communication unit 252 and the wireless communication unit 332. In this embodiment, the processing unit 3 is also communicably connected further to the radiation source control unit 4, the display 6, and the input terminal 7 by the communication unit 33.

The radiation source control unit 4 can control or drive the radiation source 1 based on a signal from the processing unit 3. The irradiation switch 5 is connected to the radiation source control unit 4, and a user such as a doctor can input a signal indicating an image capturing start request by pressing the irradiation switch 5.

The display 6 and the input terminal 7 are connected to the processing unit 3 (by the communication unit 33 in this embodiment) and can exchange signals with the processing unit 3. A known display such as a liquid crystal display can be used as the display 6. A known element such as a keyboard or mouse can be used as the input terminal 7.

With the above arrangement, the radiation imaging apparatus AP can perform radiation image capturing (to be also simply referred to as "image capturing" in this specification) of the object OB. Although details will be described later, the outline of the operation in each element when performing image capturing is as follows.

First, the user inputs image capturing conditions necessary for image capturing to the processing unit 3 using the input terminal 7. Examples of the image capturing conditions are information (a name, an age, a tissue or portion as the image capturing target, and the like), an image capturing mode (a still image mode, a moving image mode, or the like), parameters (the irradiation intensity and irradiation time of radiation, a frame rate, and the like), and the like. After that, when the user presses the irradiation switch 5, the radiation source control unit 4 outputs a notification signal indicating this to the processing unit 3. The processing unit 3 communicates with the image capturing unit 2 and determines based on a response from the image capturing unit 2 whether image capturing is possible.

If it is determined that the start of the image capturing is possible, the processing unit 3 sets the driving or control timing of each element so that the image capturing is appropriately implemented by the image capturing unit 2 (scheduling). More specifically, the processing unit 3 generates a driving signal so that the radiation source 1 can start and end radiation irradiation at appropriate timings. This driving signal is transmitted from the processing unit 3 to the radiation source 1 via the radiation source control unit 4, and the radiation source 1 generates radiation based on this driving signal.

The radiation enters the image capturing unit 2 via the object OB. The image capturing unit 2 causes the sensor array 21 to detect the radiation and generates image data based on the detection result. The processing unit 3 receives the image data from the image capturing unit 2, then performs predetermined image processing, as needed, and displays a radiation image based on this image data on the display 6. The user can perform the observation or diagnosis of the image capturing target based on this radiation image.

Note that the system arrangement of the radiation imaging apparatus AP is not limited to the example in FIG. 1, but various changes in the arrangement are possible, as needed, without departing from the scope of the present invention. For example, other elements may be added to this arrangement, and some elements may be replaced or omitted. Alternatively, some or all of the functions of some elements may be arranged in other elements. For example, the radiation source control unit 4 may be arranged as some elements of the radiation source 1 or some elements of the processing unit 3, and the display 6 and/or the input terminal 7 may be arranged as some elements of the processing unit 3.

FIG. 2 is a view for explaining an example of a method of performing synchronization between the image capturing unit 2 and the processing unit 3. In FIG. 2, the abscissa serves as the time axis and indicates a measurement value (the measurement result by the timer unit 32 corresponds to time for the processing unit 3) CL0 of the timer unit 32 on the side of the processing unit 3 and a measurement value (the measurement result by the timer unit 25 corresponds to time for the image capturing unit 2) CL1 of the timer unit 25 on the side of the image capturing unit 2. For example, when the image capturing unit 2 and the processing unit 3 are communicably connected to each other by the communication unit 26 and the communication unit 33, the measurement value CL1 of the timer unit 25 is made to match the measurement value CL0 of the timer unit 32 in order to perform synchronization between the image capturing unit 2 and the processing unit 3.

In this case, as soon as the image capturing unit 2 and the processing unit 3 are connected to each other, the measurement value CL0 and the measurement value CL1 do not match each other. For example, if CL0=10250 in the processing unit 3, CL1=10253 in the image capturing unit 2. The image capturing unit 2 requests the time information (information of the measurement value CL0) of the timer unit 32 to the processing unit 3 at a predetermined timing after the image capturing unit 2 and the processing unit 3 are connected, that is, at a timing of CL1=10254. This request is indicated by a "request A" in FIG. 2.

The processing unit 3 receives the request A at the timing of CL0=10254 and replies, to the image capturing unit 2, the time information (information of the measurement value CL0) of the timer unit 32 in response to the request A. This reply is indicated by a "reply B" in FIG. 2. After that, the image capturing unit 2 receives the reply B at the timing of CL1=10260.

Upon reception of the reply B, the image capturing unit 2 can change the measurement value CL1 of the timer unit 25 based on the timing of transmission of the request A, the timing of reception of the reply B, and the timing of the response of the processing unit 3 (the timing at which the processing unit 3 receives the request A and transmits the reply B). In general, the time required for communication from the image capturing unit 2 to the processing unit 3 is almost equal to the time required for communication from the processing unit 3 to the image capturing unit 2. The intermediate timing, that is, CL0=10257, between the timing (CL1=10254) at which the image capturing unit 2 transmits the request A and the timing (CL1=10260) at which the image capturing unit 2 receives the reply B corresponds the timing of the response of the processing unit 3, that is, CL0=10254. Accordingly, the image capturing unit 2 can measure (or expressed as specify or calculate) a difference of the measurement value CL1 of the timer unit 25 from the measurement value CL0 of the timer unit 32 of the processing unit 3, that is, the time difference between the timer units 25 and 32. In this example, the time difference is "−3". In this embodiment, the measurement value CL1 is changed to CL1=10259 using the measured time difference "−3" as the correction value at the timing of CL1=10262, thereby completing synchronization.

Typically, the processing unit 3 and the radiation source control unit 4 are connected via a cable, the radiation source 1 and the radiation source control unit 4 are connected via a cable, and these units can perform communication by directly exchanging electrical signals. On the other hand, many portable cassette type units can be used as the image capturing unit 2. In a hospital or the like, the processing unit 3 is selectively connected to one of the plurality of image capturing units 2. The image capturing unit 2 and the processing unit 3 can be connected by wired or wireless communication. The processing information of the image capturing unit 2 (mainly the image capturing control unit 24) and the processing information of the processing unit 3 (mainly the arithmetic operation unit 31) can be converted into data (a command, a message, or the like) complying with the communication methods of the image capturing unit 2 and the processing unit 3 and communicated in order to implement data exchange between the image capturing unit 2 and the processing unit 3. In many cases, the communication rate between the image capturing unit 2 and the processing unit 3 is lower (that is, the response time is long) than the transmission rate of the driving signal from the processing unit 3 to the radiation source 1. The communication rate (or the response time) between the image capturing unit 2 and the processing unit 3 readily varies depending on the communication state or communication environment.

This may become a cause by which the driving timing of the image capturing unit 2 accidentally varies with respect to the driving timing of the radiation source 1. For example, this may become a cause by which radiation irradiation by the radiation source 1 may be started before the image capturing unit 2 is set in the image capturing enable state. In order to appropriately perform radiation image capturing, the processing unit 3 is required to perform driving or control scheduling of each element of the radiation imaging apparatus AP in consideration of the response time in the communication between the image capturing unit 2 and the processing unit 3.

Figure 3A:
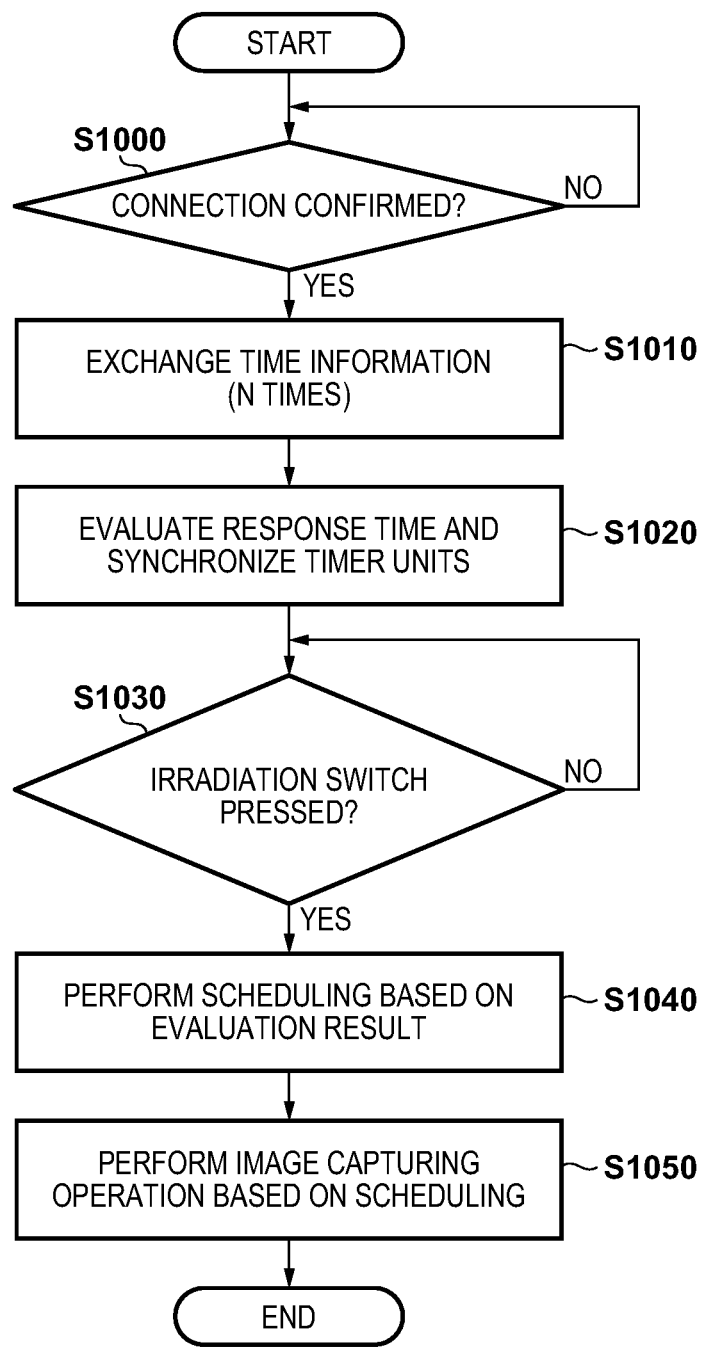
FIGS. 3A, 3B, 3C, and 3D are flowcharts for explaining an example of a scheduling mode.

Scheduling in consideration of the response time in the communication between the image capturing unit 2 and the processing unit 3 will be described with reference to FIGS. 3A to 3D. FIG. 3A is a flowchart for explaining an overall operation in the radiation imaging apparatus AP. As an outline, first the response times of the image capturing unit 2 and the processing unit 3 are evaluated in accordance with the confirmation of the connection between them, and the image capturing unit 2 and the processing unit 3 are synchronized with each other. In response to pressing of the irradiation switch 5 by the user, scheduling is performed based on the evaluation result of the response times. After that, the image capturing operation is performed based on the scheduling result.

Scheduling here is to set driving or control timings of the radiation source 1 and the image capturing unit 2 so as to appropriately implement radiation image capturing by the radiation imaging apparatus AP. These timings depend on mainly the communication state between the image capturing unit 2 and the processing unit 3 in addition to the image capturing conditions input by the user using the input terminal 7 in this embodiment. Details will be described later, but the following items are considered in this scheduling:

after the irradiation switch 5 is pressed, whether the image capturing unit 2 is set in an image capturing enable state within a predetermined time, after the image capturing unit 2 is set in the image capturing start enable state, what timing is the radiation source 1 driven and controlled? and after the image capturing unit 2 is set in the image capturing start enable state, what timing is the image capturing unit 2 driven and controlled?

In step S1000 (to be referred to as simply "S1000"; this also applies to other steps), the process advances to S1010 in response to the confirmation that the image capturing unit 2 and the processing unit 3 are connected. The connection confirmation can be implemented by detecting access by wired communication using a LAN cable or wireless communication using Wi-Fi using, for example, a known connection detection sensor.

In S1010, exchange of time information is performed between the image capturing unit 2 and the processing unit 3. More specifically, transmission/reception of the request A and the reply B described with reference to FIG. 2 is performed. As described above, since the communication rate (that is, the response time) between the image capturing unit 2 and the processing unit 3 varies depending on the communication state, the transmission/reception of the request A and the reply B is performed a plurality of times (N times for N>2).

In S1020, the response time in the communication between the image capturing unit 2 and the processing unit 3 is evaluated based on the result in S1010. According to this embodiment, a time required for transmission/reception of the requests A and the replies B of a plurality of times (the time from transmission of each request A to the reception of the replay corresponding to this request) is measured, and the response time is evaluated based on the average value of the plurality of measurement results.

Simultaneously with the evaluation of the response time, in S1020 the image capturing unit 2 and the processing unit 3 are synchronized based on the result of S1010. That is, the measurement value CL1 of the timer unit 25 of the image capturing unit 2 is corrected. In this embodiment, as described with reference to FIG. 2, the time difference between the measurement values CL0 and CL1 for each transmission/reception of the requests A and the replies B of the plurality of times is measured, and the measurement value CL1 is corrected using the average value of the plurality of measurement results as the correction value.

After that, in S1030, the process advances to S1040 in response to pressing of the irradiation switch 5 by the user. Details will be described later. In S1040, scheduling is performed based on the evaluation result of the response time obtained in S1020. In S1050, the image capturing operation is performed based on the scheduling result.

Figure 3B:
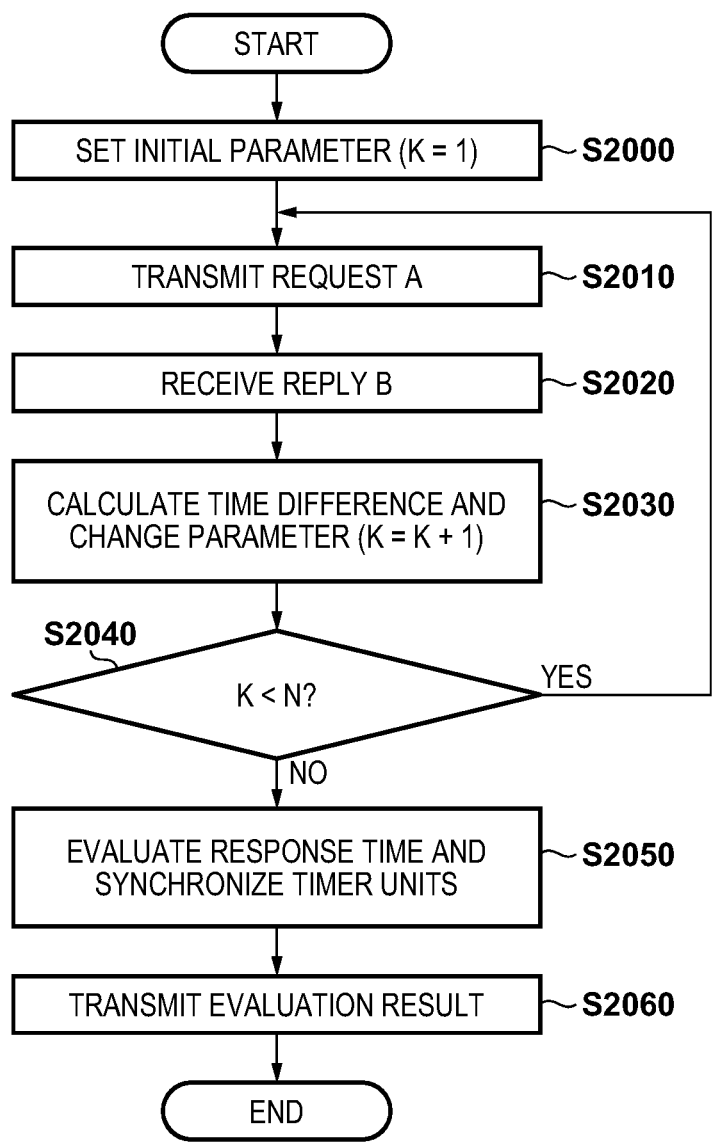

FIG. 3B is a flowchart for explaining an operation corresponding to S1010 to S1020 in the image capturing unit 2 after the connection with the processing unit 3 is confirmed. The contents of the flowchart are mainly performed by the image capturing control unit 24. As an outline, the image capturing unit 2 confirms the connection with the processing unit 3, evaluates the response time between the image capturing unit 2 and the processing unit 3, and then the image capturing unit 2 and the processing unit 3 are synchronized. The image capturing unit 2 also transmits the response time evaluation to the processing unit 3.

In S2000, after the connection with the processing unit 3 is confirmed, the initial value of at least one parameter including K is set. In this case, K is the parameter for evaluating the response time between the image capturing unit 2 and the processing unit 3, and K=1 is set. Note that as other parameters, for example, a parameter based on the image capturing condition input by the user using the input terminal 7, a parameter unique to the image capturing unit 2 and/or the processing unit 3, a parameter necessary for other image capturing, and the like are enumerated.

In S2010, the request A is transmitted to the processing unit 3. The request A is data (a command, a message, or the like) representing that the time information (information of the measurement value CL0) of the timer unit 32 is requested. The data is output in the data format complying with the communication method between the image capturing unit 2 and the processing unit 3. In this case, according to this embodiment, the time information (information of the measurement value CL1) of the timer unit 25 of the image capturing unit 2 is written in the data as the request A. That is, it is assumed that the request A includes the time information (information of the measurement value CL1) of the timer unit 25.

The processing unit 3 transmits the reply B to the image capturing unit 2 in response to the reception of the request A. The reply B is data (a command, a message, or the like) including the time information (information of the measurement value CL0) of the timer unit 32 and is output in the data format complying with the communication method between the image capturing unit 2 and the processing unit 3. The time information (information of the measurement value CL0) of the timer unit 32 is further written as the reply to the request A in the data serving as the reply B. That is, the reply B includes the time information (information of the measurement value CL1) of the timer unit 25 and the time information (information of the measurement value CL0) of the timer unit 32. The image capturing unit 2 receives the reply B from the processing unit 3, and this step is set to S2020.

In S2030, the time difference (a shift amount between the measurement values CL1 and CL0) between the timer units 25 and 32 based on the reply B is measured. More specifically, first, as described with reference to FIG. 2, intermediate time between the time (the measurement value CL1) of transmission of the request A by the image capturing unit 2 and the time (the measured value CL1) of reception of the reply B by the image capturing unit 2 is obtained. After that, the difference between this intermediate time and the time (the measurement value CL0) of the transmission of the reply B by the processing unit 3 is measured. Since the information indicating the time (measurement value CL1) of the transmission of the request A by the image capturing unit 2 and the time (measurement value CL0) of the transmission of the reply B by the processing unit 3 are written in the data as the reply B, the image capturing unit 2 can perform the measurement operation. After that, 1 is added to the parameter K set in S2000 (K=K+1).

Note that as another embodiment, information indicating the time (measurement value CL1) of the transmission of the request A by the image capturing unit 2 may be temporarily held in a memory in the image capturing unit 2. Accordingly, the above measurement operation of S2030 can be implemented.

Although details will be described later, the difference between the time (measurement value CL1) of transmission of the request A by the image capturing unit 2 and the time (measurement value CL1) of reception of the reply B by the image capturing unit 2 is measured as the response time in one communication between the image capturing unit 2 and the processing unit 3.

It is determined in S2040 whether the parameter K satisfies K<N. If K<N, then the process returns to S2010; otherwise (K N), the process advances to S2050. Accordingly, the measurement operation described with reference to S2010 to S2030 is performed N times. That is, the measurement operation of the time difference (the shift amount between the measurement values CL1 and CL0) between the timer units 25 and 32 and the measurement operation of the response time in the communication between the image capturing unit 2 and the processing unit 3 are performed N times each.

In S2050, the response time between the image capturing unit 2 and the processing unit 3 is evaluated based on the N-time measurement results obtained in S2010 to S2040. In addition, the timer units 25 and 32 are synchronized. The response time evaluation is performed based on N-time average value of differences each between the time (measurement value CL1) of the transmission of the request A by the image capturing unit 2 and the time (measurement value CL1) of reception of the reply B by the image capturing unit 2. In addition, the synchronization between the timer units 25 and 32 is performed based on the N-time average value of the time differences (shift amounts between the measurement values CL1 and CL0). The measurement value CL1 of the timer unit 25 is corrected based on this average value.

In S2060, the response time evaluation result obtained in S2050 is transmitted to the processing unit 3, and this flowchart ends. The evaluation result will be described in detail later. However, the evaluation result is used when the processing unit 3 sets the driving or control timings of the radiation source 1 and the image capturing unit 2, that is, when scheduling is performed.

Figure 3C:
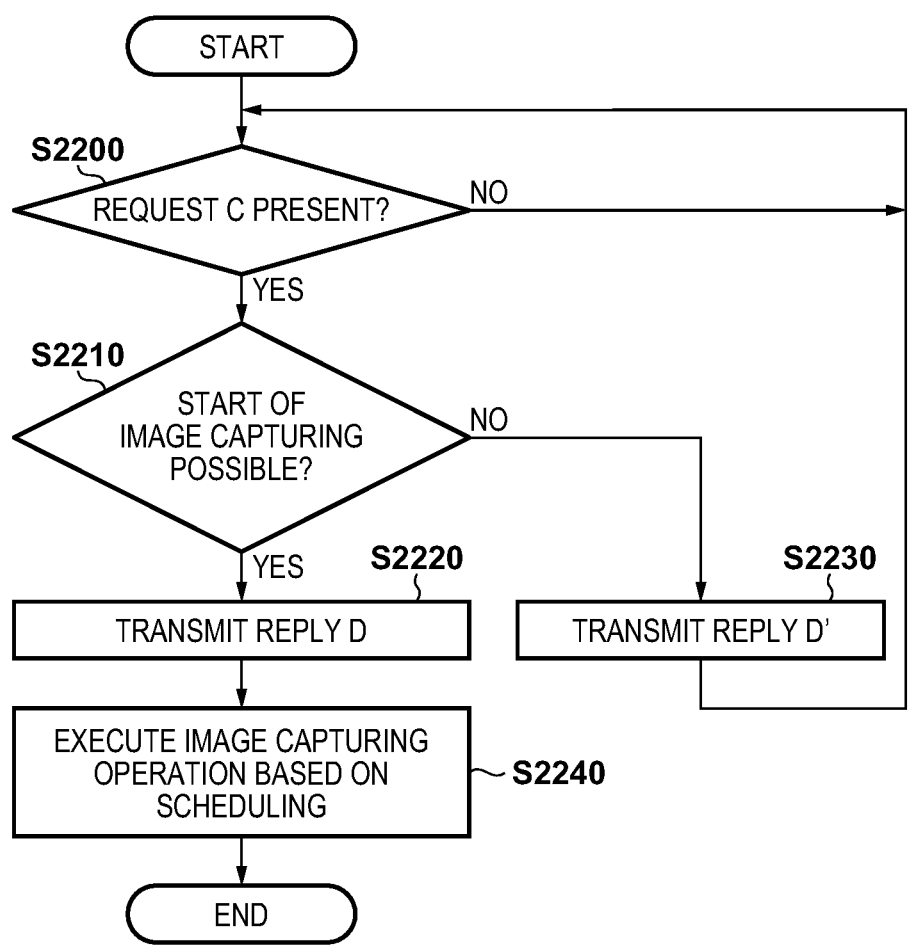

FIG. 3C is a flowchart for explaining the operation corresponding to S1030 to S1050 in the image capturing unit 2 upon completion of synchronization with the processing unit 3. The contents of this flowchart can mainly be performed by the image capturing control unit 24. As an outline, the image capturing unit 2 receives an image capturing start request (to be referred to as a "request C") from the processing unit 3 in response to pressing of the irradiation switch 5, determines whether the start of the image capturing is possible, and replies the determination result (to be referred to as a "reply D"). If the start of the image capturing is possible, the image capturing unit 2 performs an image capturing operation based on scheduling according to the request C.

Upon reception of the request C in S2200, it is determined in S2210 whether the image capturing in a desired image capturing mode can be started at desired expected time (or within the predetermined time). The request C is data (a command, a message, or the like) in which the above image capturing mode and the expected time are written and is output in a data format complying with the communication method between the image capturing unit 2 and the processing unit 3. If the image capturing operation based on the request C is possible, the process advances to S2220; otherwise, the process advances to S2230.

In this case, examples of the image capturing mode are a still image mode, a moving image mode, and a continuous image capturing mode. The image capturing mode can be set based on the image capturing conditions input by the user using the input terminal 7. In addition, the expected time indicates the expected time of the start of the image capturing operation by the image capturing unit 2 and is given by, for example, CL0=CL1=Tx (Tx: arbitrary time). The expected time of the start of the image capturing operation can be set based on the evaluation result (see S1020 and S2050) of the response time and/or the above image capturing conditions.

In S2220, the reply D is transmitted to the processing unit 3 as the data indicating that the stat of the image capturing operation is possible at the expected time Tx in the set image capturing mode, and the process advances to S2240. On the other hand, in S2230, a reply D' is transmitted to the processing unit 3 as the data indicating that the start of the image capturing operation is impossible. The process then returns to S2200. The replies D and D' are output in a data format (a command, a message, or the like) complying with the communication method between the image capturing unit 2 and the processing unit 3.

In S2240, the image capturing operation is performed based on scheduling according to the request C. Although details will be described later, the image capturing operation by the image capturing unit 2 includes a preparation operation, an accumulation operation, and a readout operation.

Figure 3D:
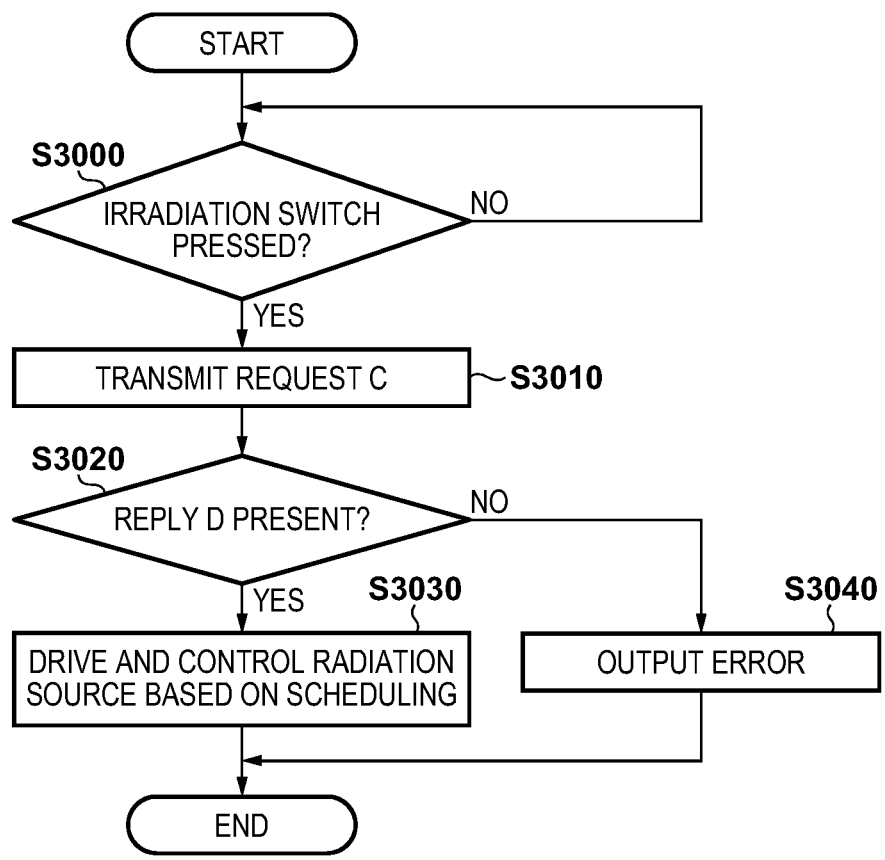

FIG. 3D is a flowchart for explaining the operation of the processing unit 3 after the evaluation result of the response time described above (see S2010 to S2050) is received from the image capturing unit 2. The contents of this flowchart can mainly be performed by the arithmetic operation unit 31.

As an outline, the processing unit 3 outputs the request C (see S2200) to the image capturing unit 2 in response to pressing of the irradiation switch 5. If the reply D is received from the image capturing unit 2, the driving signal is output to the radiation source 1 based on scheduling according to the request C, thereby starting/ending radiation irradiation.

In response to the pressing of the irradiation switch 5 by the user in S3000, the request C is transmitted to the image capturing unit 2 in S3010. As described above, the request C is data which requests to start image capturing in the desired image capturing mode at the desired expected time Tx. In other words, from the viewpoint of the processing unit 3, the request C can be said as data for sending an inquiry to the image capturing unit 2 to determine whether scheduling based on the evaluation result (see S1020 and S2050) and/or the image capturing conditions input by the user is allowed.

In S3020, if the reply D is received in response to the request C in S3010 (if the data indicating that the start of the image capturing is possible), the process advances to S3030; otherwise (the reply D', that is, if the data indicating that the start of image capturing is impossible), the process advances to S3040.

In S3030, since the reply D (that is, the data indicating that the start of image capturing is possible), scheduling according to the request C is performed assuming that the request C is received by the image capturing unit 2. The driving signal for driving the radiation source 1 is generated.

In S3040, since the reply D' (that is, the data indicating that the start of image capturing is impossible) is received, for example, an error output is performed to the display 6 assuming that the request C is not received by the image capturing unit 2. At this time, the processing unit 3 may cause the display 6 to display a message indicating that the start of image capturing is impossible and information accessory to this message (for example, a message indicating that the image capturing conditions should be changed and a message indicating that the communication state between the image capturing unit 2 and the processing unit 3 should be improved), thereby informing the user of this.

FIG. 4 is a view for explaining the mode of transmitting/receiving the request C and the reply D according to the flowcharts in FIGS. 3A to 3D. In FIG. 4, the abscissa serves as the time axis and indicates the measurement values CL0 and CL1 of the synchronized timer units 32 and 25, and at the same time the state of the irradiation switch 5, the radiation irradiation amount by the radiation source 1, and the operating state of the image capturing unit 2.

During high level (H level) of the irradiation switch 5, the irradiation switch 5 is set in the pressed state. During low level (L level) of the irradiation switch 5, the irradiation switch 5 is set in the unpressed state.

During H level, the radiation irradiation amount is set in a state in which the radiation source 1 is driven, that is, in a state in which the image capturing unit 2 is irradiated with the radiation. During L level, the radiation irradiation amount is set in a state in which above driving is suppressed, that is, in a state in which the image capturing unit 2 is not irradiated with the radiation.

The examples of the operating state of the image capturing unit 2 are mainly the preparation operation, the accumulation operation, and the readout operation in this embodiment. In a period other than the above operations, the image capturing unit 2 is set in a stopped state. Although details will not be described, in the preparation operation, each sensor S of the sensor array 21 is driven in a predetermined period by the driving unit 22 and thus initialized (see FIG. 1). Along with the elapse of the time, a noise component generated in each sensor S is removed. In addition, in the accumulation operation, the charges generated upon radiation irradiation are accumulated in each sensor S. In the readout operation, each sensor is driven by the driving unit 22, and the readout unit 23 reads out, from each sensor S as a sensor signal, an electrical signal corresponding to the charges accumulated in the above accumulation operation. The image capturing control unit 24 generates image data based on the readout sensor signal.

The processing unit 3 transmits the request C to the image capturing unit 2 at, for example, the time CL0 (=CL1) =20100 in response to pressing (see S3000) of the irradiation switch 5 (see S3010). As an example, the unit of the abscissa is assumed to be msec. In this case, the processing unit 3 sends an inquiry to the image capturing unit 2 to determine whether scheduling for performing the moving image mode in which the radiation irradiation of the irradiation period of 50 msec is repeated in a period of 150 msec from the expected time Tx=20300 is possible.

The image capturing unit 2 receives the request C at the time CL1 (CL0)=20150 (see S2200) and determines whether scheduling according to the request C is possible (see S2210). In the case of the request C, the image capturing unit 2 completes the preparation operation until at least CL1=Tx (=20300). At this time, a state in which the start of the accumulation operation is possible must be set. In this embodiment, the image capturing unit 2 determines whether scheduling according to the request C is possible and transmits the reply D (that is, the data indicating that the start of the image capturing is possible) to the processing unit 3 (see S2220).

The processing unit 3 receives the reply D at the time CL0 (=L1)=20200 (see S3020). Accordingly, the image capturing unit 2 can determine that the accumulation operation is started from the expected time Tx=20300. After that, the processing unit 3 generates the driving signal according to the request C and outputs it to the radiation source 1 via the radiation source control unit 4, thereby implementing scheduling according to the request C.

The image capturing unit 2 starts the preparation operation at, for example the time CL1=20200, completes the preparation operation until the time CL1=Tx (=20300), and starts the accumulation operation. The processing unit 3 outputs the driving signal to the radiation source 1 at the time CL0=Tx (=20300), starts the radiation irradiation, and ends the radiation irradiation at the time CL0=20350. After that, the image capturing unit 2 completes the readout operation until the time CL1=20450 at which the next radiation irradiation is started, thereby obtaining image data of one frame.

In this manner, a series of operations, that is, the radiation irradiation, the accumulation operation, and the readout operation are repeated in a period of 150 msec, thereby generating moving image data based on the image data of a plurality of frames thus obtained.

Note that the transmission rate of the driving signal from the processing unit 3 to the radiation source 1 is higher (a shorter response time) than the communication rate between the image capturing unit 2 and the processing unit 3. In this embodiment, the transmission delay of the driving signal is substantially absent.

As described above, the response time between the image capturing unit 2 and the processing unit 3 readily varies depending on the communication state. For example, if the communication between the image capturing unit 2 and the processing unit 3 is implemented by wireless communication, this response time readily varies as compared with a case in which the communication is implemented by wired communication (the variation amount of the communication rate is large). For this reason, in the case of the wireless communication, as compared to the wired communication, it is assumed that a relatively large delay tends to occur in the communication between the image capturing unit 2 and the processing unit 3, for example, a large delay tends to occur as compared with the evaluation result of the response time (see S1020 and S2050). In this case, an unexpected operation sequence may occur (for example, the order of driving control of the radiation source 1 and the image capturing unit 2 is reversed). So-called invalid irradiation may occur. Note that this may occur even in the wired communication due to external noise or the like.

In order to prevent invalid irradiation, the scheduling by the processing unit 3 may be adjusted based on whether the communication between the image capturing unit 2 and the processing unit 3 is wired or wireless communication. This will be described below with reference to FIGS. 5 and 6.

Figure 5:
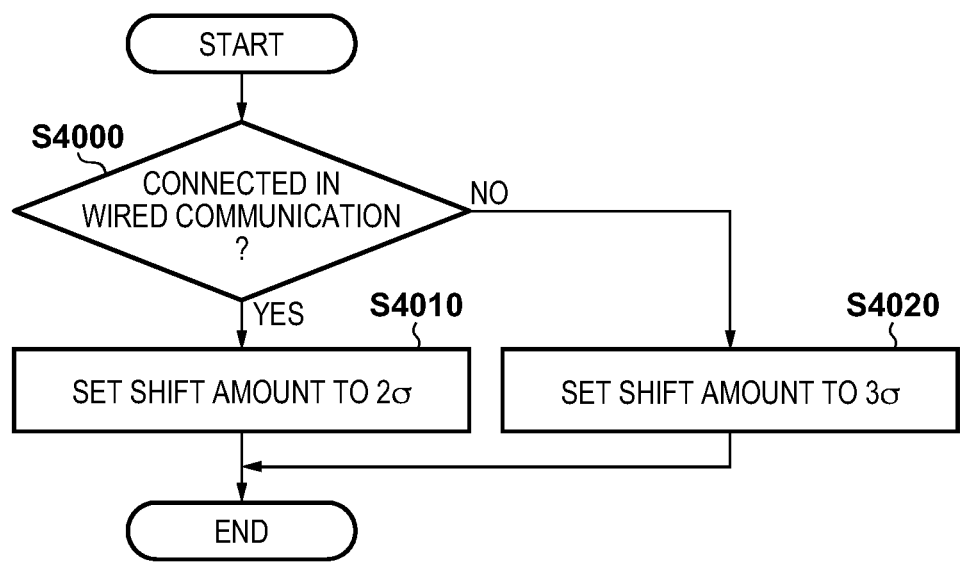
FIG. 5 is a flowchart for explaining an example of a scheduling mode.

FIG. 5 is a flowchart for explaining an example of scheduling based on the communication method between the image capturing unit 2 and the processing unit 3. In S4000, the type of communication for connecting the image capturing unit 2 and the processing unit 3 is determined. If the communication is wired communication, the process advances to S4010; otherwise (if the communication is wireless communication), the process advances to S4020.

In S4010 and S4020, the driving timings of the radiation source 1 are shifted. More specifically, the start timing of radiation irradiation and the end timing of the radiation irradiation are shifted. The shift amounts are changed between S4010 (wired communication) and S4020 (wireless communication). In this embodiment, a response time variation amount (standard deviation) based on the plurality of measurement results (S1010 and S2010 to S2040) obtained in evaluating the response time is defined as σ. The shift amount in S4010 is set as 2 σ, and the shift amount in S4020 is set as 3 σ.

Figure 6:
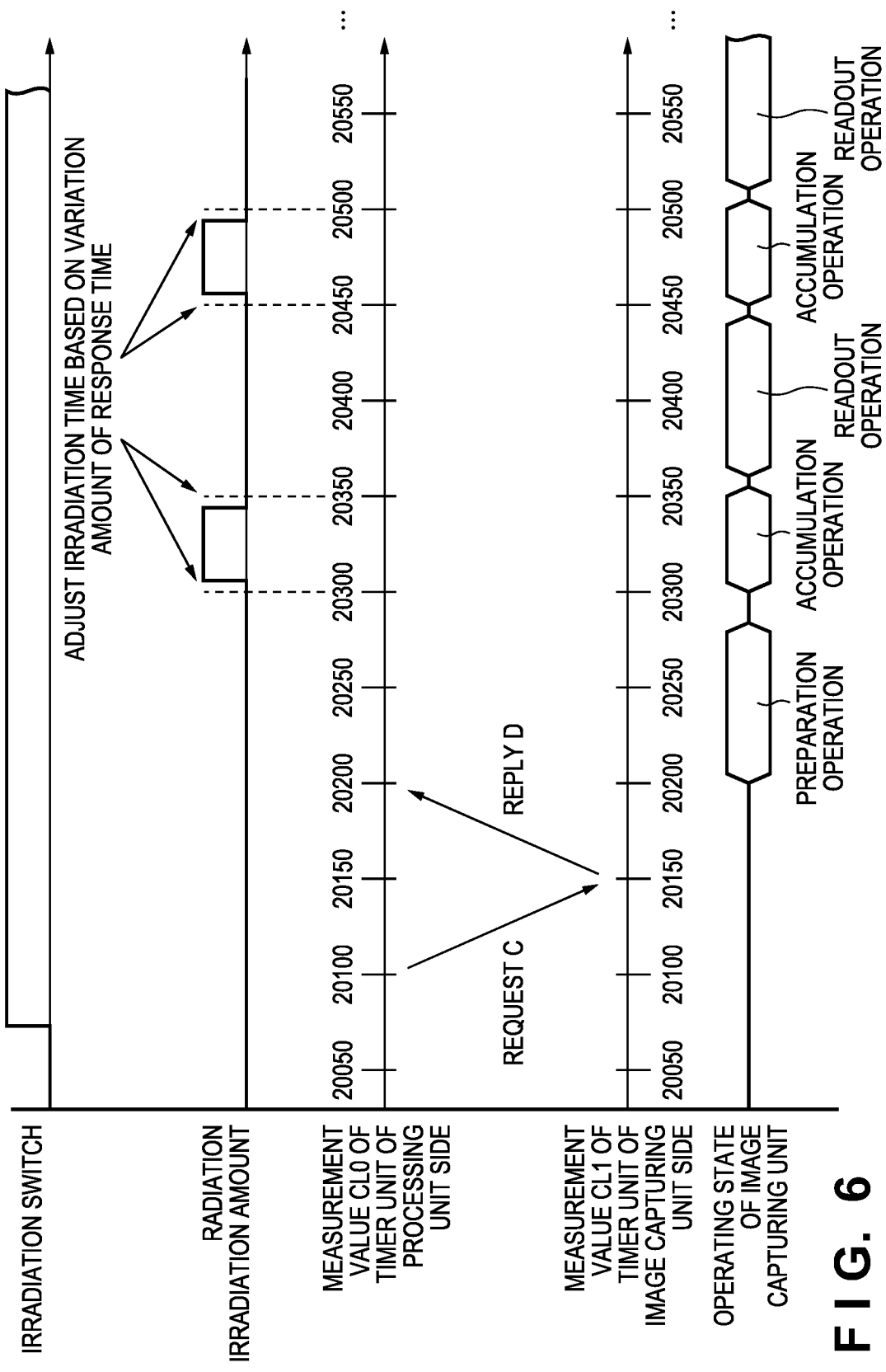
FIG. 6 is a view for explaining an example of a scheduling mode.

FIG. 6 is a view for explaining the scheduling mode based on the above flowchart as in FIG. 4. As can be obvious from FIG. 6, according to this scheduling mode, the radiation irradiation start time is shifted after the irradiation start time CL0=20300 in FIG. 4 by 2 σ in wired communication and 3 σ in wireless communication. The radiation irradiation end time is shifted before the irradiation end time CL0=20350 in FIG. 4 by 2 σ in wired communication and 3 σ in wireless communication. That is, in the case of wireless communication, the radiation irradiation start time by the radiation source 1 is delayed as compared with the case of wired communication. The radiation irradiation end time in wireless communication is advanced as compared with that in wired communication. As a result, in the case of wireless communication, the radiation irradiation time by the radiation source 1 can be made shorter than that in the case of wired communication.

According to the above scheduling mode, the irradiation time capable of suppressing invalid irradiation can be appropriately set in consideration of the response time variation amount in accordance with the type of communication between the image capturing unit 2 and the processing unit 3. Accordingly, the driving control of the radiation source 1 and the image capturing unit 2 can be performed in an appropriate order such that the start of the radiation irradiation by the radiation source 1 is not performed before the start of the accumulation operation of the image capturing unit 2 and the end of radiation irradiation is not performed after the end of the accumulation operation of the image capturing unit 2.

Note that the shift amount 2 σ or 3 σ is sufficiently small as compared with the irradiation time of one cycle (in this embodiment, about 50 msec) and has a sufficiently small influence on the obtained image data of one frame.

At a relatively high frame rate, it is difficult to set a time margin in scheduling by the processing unit 3. For this reason, for example, if image capturing in the moving image mode is performed at a relatively high frame rate, wired communication advantageous in the communication rate and the above scheduling is used.

The mode in which scheduling is performed based on the type of communication between the image capturing unit 2 and the processing unit 3 has been exemplified. However, as another example, the shift amount may be adjusted based on the communication response time evaluation regardless of the type of communication.

As described above, according to this embodiment, the processing unit 3 evaluates the response time in the communication with the image capturing unit 2, and the control timing of the radiation source 1 is set based on this evaluation result. For this reason, according to this embodiment, an unexpected event in which the radiation source 1 is driven before the image capturing unit 2 is set in the image capturing enable state can be prevented. The radiation source 1 can be driven at an appropriate timing. Therefore, according to this embodiment, the radiation image capturing can appropriately be implemented.

Several preferred embodiments have been described above, but the present invention is not limited to these. Some of the embodiments may be changed within the range without departing the scope of the present invention. For example, some of the contents of another embodiment may be combined with the contents of a given embodiment. Alternatively, known elements may be further added or omitted, as needed.

For example, in the above embodiment, when evaluating the response time between the image capturing unit 2 and the processing unit 3, or establishing synchronization (synchronization between the timer units 25 and 32), a mode using an average value of N-time measurement results (see S1010 and S2010 to S2040) has been exemplified, but the present invention is not limited to this. For example, as another embodiment, a standard deviation, a minimum value, a median value, or a combination including these (including the average value) of the N-time measurement results may be used. In addition, some of the N-time measurement results may be used, and all the N-time measurement results need not be used. For example, the N-time measurement results may be sorted in ascending order of the times (so-called round trip time) each required from the transmission of the request A to the reception of the reply B. Among the sorted measurement results, a predetermined number of measurement results having shorter times may be referred to. In addition, when synchronizing the image capturing unit 2 and the processing unit 3, a correction value may be calculated based on the predetermined number of measurement results. In addition, the least-square approximation method may be used in this calculation.

In addition, in the above embodiment, the above synchronization is to correct the measurement value CL1 of the timer unit 25 so as to match the measurement value CL0 of the timer unit 32, that is, the measurement value CL0 of the timer unit 32 is used as the reference. This relationship may be reversed. That is, as another embodiment, the above synchronization may be implemented such that the measurement value CL0 of the timer unit 32 is made to match the measurement value CL1 of the timer unit 25. In addition, in the above embodiment, the synchronization mode by the communication between the image capturing unit 2 and the processing unit 3 has been exemplified. However, the synchronization mode is not limited to this. For example, the above synchronization may be performed by receiving the common time information from, for example, a base station or a public facility.

As for transmission/reception of the request A and the reply B between the image capturing unit 2 and the processing unit 3, as another embodiment, the processing unit 3 may transmit the request A to the image capturing unit 2 and may receive the reply B from the image capturing unit 2. That is, the above evaluation and synchronization may be implemented by transmitting the request A from one of the image capturing unit 2 and the processing unit 3 to the other and transmitting the reply B from the other on the receiving side to one. Alternatively, out of the image capturing unit 2 and the processing unit 3, one which has evaluated the response time notifies the other of the result. Therefore, the evaluation result of the response time may be shared between the image capturing unit 2 and the processing unit 3.

In addition, when the image capturing unit 2 and the processing unit 3 are fixedly connected, the timer units 25 and 32 need not be individually arranged. One of the timer units 25 and 32 may be shared between the image capturing unit 2 and the processing unit 3.

In addition, if the response time in the communication between the image capturing unit 2 and the processing unit 3 is specified, the processing unit 3 can decide a specific timing at which the radiation source 1 and the image capturing unit 2 are driven and controlled. That is, scheduling becomes possible. In other words, the processing unit 3 can decide that the radiation irradiation by the radiation source 1 is started/ended and the operation is shifted to the preparation operation/accumulation operation/readout operation of the image capturing unit 2 after a specific time has elapsed from the timing at which the irradiation switch 5 is pressed. For this reason, synchronization between the image capturing unit 2 and the processing unit 3 is not essential.

In addition, there is no substantial transmission delay of the driving signal from the processing unit 3 to the radiation source 1. If the transmission delay becomes relatively large, scheduling may be performed in consideration of the response time in the communication between the radiation source 1 and the processing unit 3. That is, the evaluation of the response time between the image capturing unit 2 and the processing unit 3 as described in this specification is also applicable to the evaluation of the response time between the radiation source 1 and the processing unit 3.

Embodiment(s) of the present invention can also be realized by a computer of a system or apparatus that reads out and executes computer executable instructions (e.g., one or more programs) recorded on a storage medium (which may also be referred to more fully as anon-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The individual terms described in this specification are not limited to the ones used for the purpose of the description of the present invention. In the present invention, the terms need not be limited to the strict meanings of the terms but can include their equivalents.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-220131, filed on Nov. 15, 2017, which is hereby incorporated by reference herein in its entirety.

What is claimed is:

1. A radiation imaging apparatus, comprising:
a radiation source configured to generate radiation;
an image capturing unit comprising a sensor array, and configured to perform image capturing by detecting the radiation; and
a processing unit comprising a CPU and a memory, and configured to be communicable with the image capturing unit, wherein the processing unit performs:
a first operation which evaluates a response time in a communication with the image capturing unit,
a second operation which sets a control timing of the radiation source based on an evaluation result of the response time obtained in the first operation, and
a measurement operation of the response time a plurality of times and evaluates the response time based on a plurality of measurement results obtained by the measurement operation performed the plurality of times in the first operation.

2. The radiation imaging apparatus according to claim 1, wherein the processing unit performs the second operation based on at least one of an average value, a standard deviation, a minimum value, and a median value of the plurality of measurement results.

3. The radiation imaging apparatus according to claim 1, further comprising a timer unit, wherein
in the first operation, one of the processing unit and the image capturing unit transmits a first signal to the other, and the other transmits a second signal to the one in response to a reception of the first signal from the one to the other, and
the processing unit evaluates the response time based on a measurement result of the timer unit when the one transmits the first signal to the other, and a measurement result of the timer unit when the one receives the second signal from the other.

4. The radiation imaging apparatus according to claim 3, wherein the imaging capturing unit further comprises a first timer unit and the processing unit further comprises a second timer unit, and the timer unit comprises the first timer and the second timer, and
the processing unit obtains a time difference between the second timer unit and the first timer unit in the first operation based on: (i) a measurement result of one of the first timer unit and the second timer unit corresponding to the one of the processing unit and the image capturing unit, when the one transmits the first signal to the other, (ii) a measurement result of the one of the first timer unit and the second timer unit corresponding to the one of the processing unit and the image capturing unit, when the one receives the second signal from the other, and (iii) a measurement result of the other of the first timer unit and the second timer unit corresponding to the other of the processing unit and the image capturing unit, when the other receives the first signal from the one and transmits the second signal to the one.

5. The radiation imaging apparatus according to claim 1, wherein in the second operation, the processing unit sets an irradiation time of the radiation from the radiation source based on whether a communication with the image capturing unit is a wired communication or a wireless communication.

6. The radiation imaging apparatus according to claim 5, wherein in the second operation, when the communication with the image capturing unit is a wireless communication, the processing unit sets the irradiation time shorter than that in a case in which the communication with the image capturing unit is a wired communication.

7. The radiation imaging apparatus according to claim 5, wherein in the second operation, the processing unit delays an irradiation start time of the radiation from the radiation source when the communication with the image capturing unit is a wireless communication as compared to when the communication with the image capturing unit is a wired communication, and
the processing unit advances an irradiation end time of the radiation by the radiation source when the communication with the image capturing unit is a wired communication.

8. The radiation imaging apparatus according to claim 1, wherein the processing unit is configured to be communicable with the radiation source, and further evaluates a response time in a communication with the radiation source in the first operation, and
in the second operation, the processing unit sets a control timing of the radiation source based on an evaluation result of the response time in a communication with the image capturing unit and an evaluation result of the response time in a communication with the radiation source.

9. A radiation imaging apparatus comprising:
a radiation source configured to generate radiation;
an image capturing unit comprising a sensor array and a control unit, and configured to perform image capturing by detecting the radiation; and
a processing unit comprising a CPU and a memory, and configured to be communicable with the image capturing unit, wherein the image capturing unit performs:
a first operation which evaluates a response time in a communication with the processing unit,
a second operation which sets a control timing of the radiation source based on an evaluation result of the response time obtained in the first operation, and a measurement operation of the response time a plurality of times and evaluates the response time based on a plurality of measurement results obtained by the measurement operation performed the plurality of times in the first operation.

10. A radiation imaging apparatus comprising:

a radiation source configured to generate radiation;

an image capturing unit comprising a sensor array, and configured to perform image capturing by detecting the radiation;

an input unit comprising an input terminal, and configured to input an image capturing mode by user's operation; and a processing unit comprising a CPU and a memory, and configured to be communicable with the image capturing unit, wherein the processing unit performs:

(i) a first operation which evaluates a response time in a communication with the image capturing unit, and (ii) a second operation which sets a control timing of the radiation source and a driving timing of the image capturing unit based on an evaluation result of the response time obtained in the first operation and the input image capturing mode so that a period of a radiation irradiation by the radiation source can be set within a period of an accumulation operation of the image capturing unit.

11. The radiation imaging apparatus according to claim 10, wherein the image capturing mode includes a moving image mode with a predetermined frame rate.

12. The radiation imaging apparatus according to claim 10, wherein the image capturing unit further comprises a first timer unit and the processing unit further comprises a second timer unit, in the first operation, one of the processing unit and the image capturing unit transmits a first signal to the other, and the other transmits a second signal to the one in response to a reception of the first signal, and the processing unit evaluates the response time based on a measurement result of the first timer unit and the second timer unit when the one transmits the first signal to the other, and a measurement result of the first timer unit and the second timer unit when the one receives the second signal from the other.

13. The radiation imaging apparatus according to claim 12, wherein timings of the first timer unit and the second timer unit are synchronized by correcting a timing of the one of the first timer unit and the second timer unit to a timing of the other of the first timer unit and the second timer unit based on a time difference between the first timer unit and the second timer unit.

* * * * *